United States Patent [19]
Gross

[11] Patent Number: 5,207,648
[45] Date of Patent: May 4, 1993

[54] MULTILUMEN CATHETER

[75] Inventor: James R. Gross, Wareham, Mass.

[73] Assignee: The Kendall Company, Mansfield, Mass.

[21] Appl. No.: 932,120

[22] Filed: Aug. 19, 1992

[51] Int. Cl.⁵ .............................................. A61M 5/178
[52] U.S. Cl. .................................... 604/164; 604/280; 604/93; 604/264; 604/283
[58] Field of Search ................... 604/96–103, 604/247–249, 267, 280, 35, 40, 45; 606/191, 192, 194

[56] References Cited

U.S. PATENT DOCUMENTS

| | | | |
|---|---|---|---|
| 4,701,159 | 10/1987 | Brown et al. | 604/283 |
| 4,838,881 | 6/1989 | Bennett | 604/283 |
| 5,149,330 | 9/1992 | Brightbill | 604/264 |
| 5,156,596 | 10/1992 | Balbierz et al. | 604/264 |

Primary Examiner—C. Fred Rosenbaum
Assistant Examiner—Chalin Smith
Attorney, Agent, or Firm—Alvin Isaacs

[57] ABSTRACT

A multilumen catheter having a plurality of flexible, elongated catheter tubes concentrically and coaxially disposed, each catheter tube defining a separate lumen, each catheter tube having a distal end which extends outwardly from the distal end of the next surrounding catheter tube, and each catheter tube having a proximal end which is secured and encapsulated by a manifold which facilitates fluid communication between each of the separate lumens and fluid transfer devices or pressure monitoring devices via separate extension tubing.

18 Claims, 4 Drawing Sheets

MULTILUMEN CATHETER

FIELD OF THE INVENTION

The present invention relates to catheters and more particularly to multilumen venous catheters.

BACKGROUND OF THE INVENTION

Multilumen venous catheters are advantageous as they eliminate the need for separate catheters for monitoring a patient's blood pressure and infusing or withdrawing fluids from a patient thereby decreasing the possibility of patient discomfort and possible infection inherent with the insertion of several single lumen catheters into the patient. Maintaining fluids separately is particularly critical when the fluids employed are chemically incompatible or when cross contamination of fluids is to be avoided.

Conventional multilumen venous catheters have a plurality of lumens which may be integrally formed in a single catheter tube. The lumens in conventional multilumen catheters extend throughout the length of the catheter tube and are usually arranged in a side-by-side configuration within a catheter tube as shown in cross-section in FIG. 1. However, this configuration limits the effective cross-sectional area of each of the lumens present within the multilumen catheter as the wall sections between each of the lumens take up a significant amount of the overall area of the catheter tube. Therefore, the amount of fluid flow in each of the lumens is limited by the catheter tube diameter.

Furthermore, conventional multilumen catheters may be potentially hazardous to the patient as they provide a direct conduit for blood to leave the patient, and have been responsible for causing substantial blood loss. Some conventional multilumen catheters are equipped with extension tubing coupled to valves which close the separate lumens to blood flow when the lumens are not in use. However, these valves are not always reliable.

Another disadvantage of conventional multilumen catheters is that they are usually made in one piece from a material of limited flexibility and softness. Thus, the patient may experience increased trauma and discomfort from a relatively rigid catheter as the catheter is inserted in a vein, and damage to the inner lining of the vein may also result from such relatively rigid catheters.

Therefore, it would be desirable to have a multilumen catheter which overcomes the above-described disadvantages, which is economical to produce, and which is compatible with existing medical equipment used with conventional multiple lumen catheters.

SUMMARY OF THE INVENTION

In accordance with the present invention, disclosed is a multilumen catheter having a plurality of flexible, elongated venous catheter tubes concentrically and coaxially disposed, each catheter tube defining a separate lumen, each catheter tube having a distal end which extends outwardly from the distal end of the next surrounding catheter tube, and each catheter tube having a proximal end which is secured and encapsulated by a manifold which facilitates fluid communication between each of the lumens and separate fluid transfer devices or pressure monitoring devices via extension tubing. As will be appreciated, the catheter will be of a size, i.e. have an outer diameter, which will permit insertion in a patient's vein.

The concentric arrangement of the catheter tubes provides an efficient cross-sectional area relative to the overall cross-sectional area. Furthermore, the smallest catheter tube whose distal end extends outwardly the furthest may be made from a softer, more flexible material so as to provide an overall softer distal end of the multilumen catheter.

In one embodiment of the present multilumen catheter (FIG. 4), each of the plurality of catheter tubes has a distal end which terminates in a tapered flexible tip. The flexible tip remains closed when there is no fluid within the respective lumen thereby eliminating the possibility of substantial blood loss through the present multilumen catheter.

DESCRIPTION OF THE DRAWINGS

This invention will be more fully understood from the following solely exemplary detailed description taken in conjunction with the accompanying drawings in which.

DETAILED DESCRIPTION OF THE INVENTION

Figure 1:
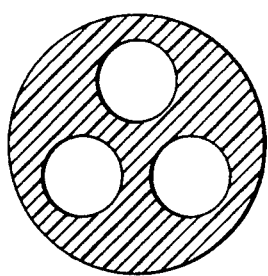
FIG. 1 is a cross-sectional view of a conventional multilumen catheter of the prior art.
Figure 2B:
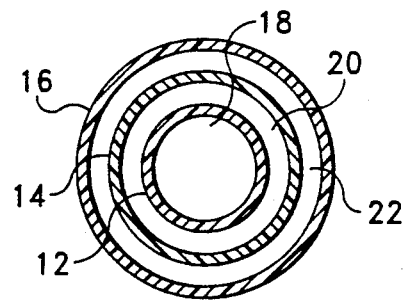
FIG. 2B is a cross-sectional view of the multilumen catheter of the present invention.
Figure 2C:
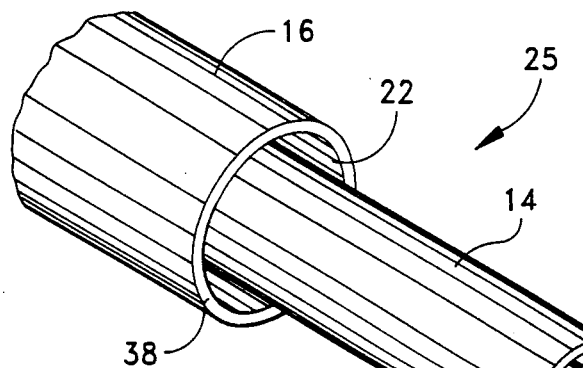
FIG. 2C a is perspective view of the distal end of the multilumen catheter shown in FIG. 2A.
Figure 2A:
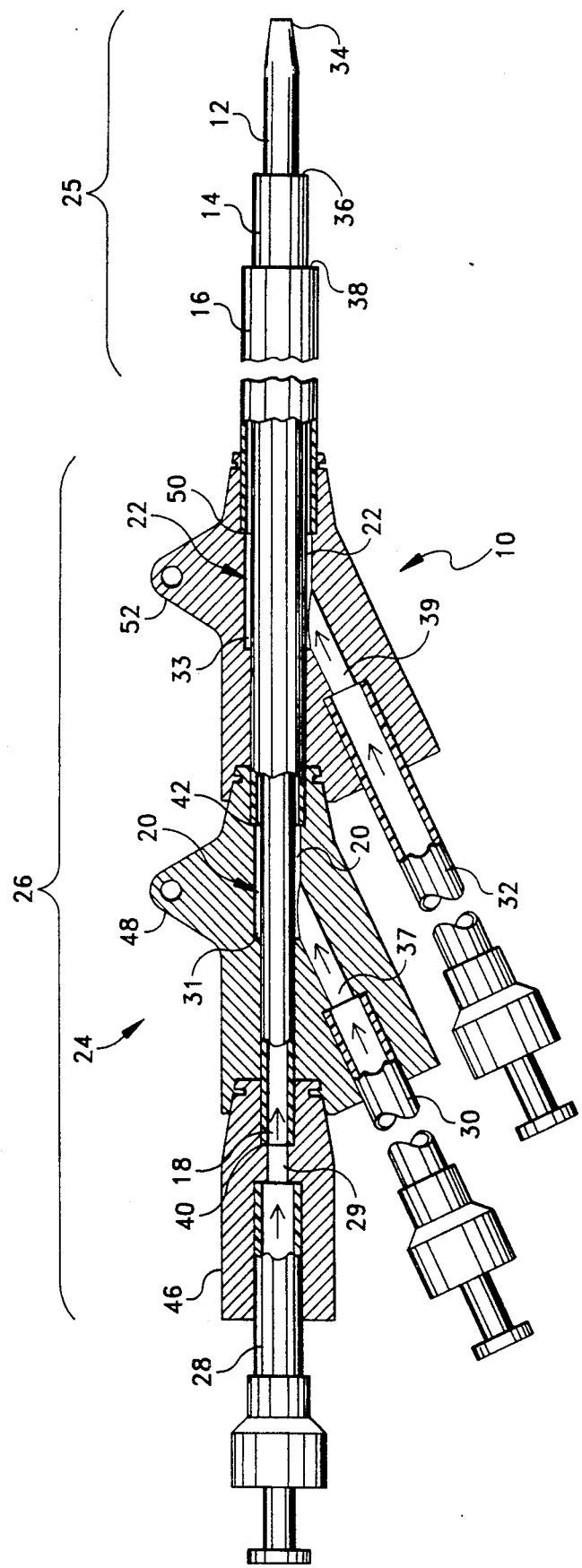
FIG. 2A is a view, partly in section, of the multilumen catheter of the present invention showing the concentrically arranged catheter tubes, their distal terminal, and the manifold.

Referring now to FIGS. 2A–2C, one embodiment of the multilumen catheter in accordance with the present invention is shown. The present multilumen catheter 10 comprises three concentrically and coaxially disposed, flexible, elongated catheter tubes 12, 14, 16, each defining separate lumens 18, 20, 22 as shown in cross-section in FIG. 2B.

The inner catheter tube 12 has a cross-section of about 0.046 in. (ID) and a wall thickness of 0.05 in; and extends longitudinally outward from the distal end 36 of the middle catheter tube 14. The middle catheter tube 14 has a cross-section of about 0.065 in. (ID), a wall thickness of 0.005 in., and extends longitudinally outward from the distal end 38 of the outer catheter tube 16. The outer tube 16 has a cross-section of about 0.82 in. (ID), and a wall thickness of 0.005 in. Accordingly, tube 12 is equivalent to a 16 gauge tube, and tubes 14 and 16 are equivalent to an 18 gauge tube.

It should be understood that more than three catheter tubes may be similarly arranged. However, for exemplary purposes, one embodiment of the present invention having three concentric lumens is shown and described in detail.

Separate lumens 18, 20, 22 terminate coextensively with the respective distal ends 34, 36, 38 of the catheter tubes 12, 14, 16. Termination of the lumens 18, 20, 22, can be more clearly seen in FIG. 2C which is a view of the distal end 25 of the multilumen catheter 10 shown in FIG. 2A.

In accordance with the invention, lumens 18, 20, 22 are independent and noncommunicative with one another, and various fluids simultaneously carried thereby do not mix prior to entering the blood stream. Furthermore, as can be clearly seen in FIG. 2C, the distal ends 34, 36, 38 of catheter tubes 12, 14, 16 are spaced apart from one another, which ensures that fluids simultaneously carried within each of the lumens 18, 20, 22 do not mix prior to being assimilated in the blood stream.

Suitable materials from which catheter tubes 12, 14, 16 may be made include flexible, sterilizable materials such as polyurethane, silicone, polyvinyl chloride (PVC) and nylon. Polyurethane is preferred. Furthermore, the inner tube 12 and the middle tube 14 may be formed from a less rigid material such as a softer, more flexible polyurethane thereby providing an overall softer distal end 25 of the multilumen catheter 10.

A softer distal end 25 is particularly desirable as it reduces trauma to the sensitive inner lining of the vein into which a multilumen catheter 10 may be inserted. Furthermore, a soft, flexible distal end 25 facilitates insertion of the catheter 10 into sinuous veins which may otherwise be difficult to access using conventional catheters having more rigid distal ends.

Referring again to FIG. 2A, the proximal end 26 of the multilumen catheter 10 includes a manifold 24 which encapsulates and secures catheter tubes 12, 14, 16 and further provides fluid communication between the lumens 18, 20, 22 and fluid transfer devices or pressure monitoring devices via separate extension tubing 28, 30, 32. Extension tubing 28, 30, 32 may be configured for attachment to fluid transfer devices or pressure monitoring devices as is known in the art. Extension tubing may be made from any suitable medical grade tubing.

As shown in the illustrative drawing, the proximal end 40 of the inner tube 12 preferably extends beyond the proximal end 42 of the middle tube 14 and is encapsulated within a hub 46 in fluid communication with extension tubing 28 via a channel 29 between the proximal end 40 of inner tube 12 and extension tubing 28. Likewise, the proximal end 42 of the middle tube 14 preferably extends beyond the proximal end 50 of the outer tube 16 and is encapsulated within a hub 48 in fluid communication with extension tubing 30 via a channel 37 communicating with an annular space 31 between the proximal end 42 of the middle tube 14 and extension tubing 30. The proximal end 50 of the outer tube 16 is encapsulated within hub 52 in fluid communication with extension tubing 32 via a channel 39 communicating with an annular space 33 between the proximal end 50 of outer tube 16 and extension tubing 32.

Each of the hubs 46, 48, 52 may be formed from a rigid, sterilizable, plastic material which can be molded using known techniques. Such materials include polycarbonate, polyurethane and PVC. The hubs 46, 48, 52, may be separately formed and then sealed together by known means to form the manifold 24.

The path of fluids flowing through the manifold 24 is indicated by arrows in FIG. 2A. Fluids flow from extension tubing 28 into the channel 29 and thereafter flow through lumen 18. Fluids flow from extension tubing 30 into the channel 37 and annular space 31 and thereafter flow around the inner tube 12 and through lumen 20. Similarly, fluids flow from extension tubing 32 into the channel 39 and annular space 33 and thereafter flow around middle tube 14 and through lumen 22.

Figure 3:
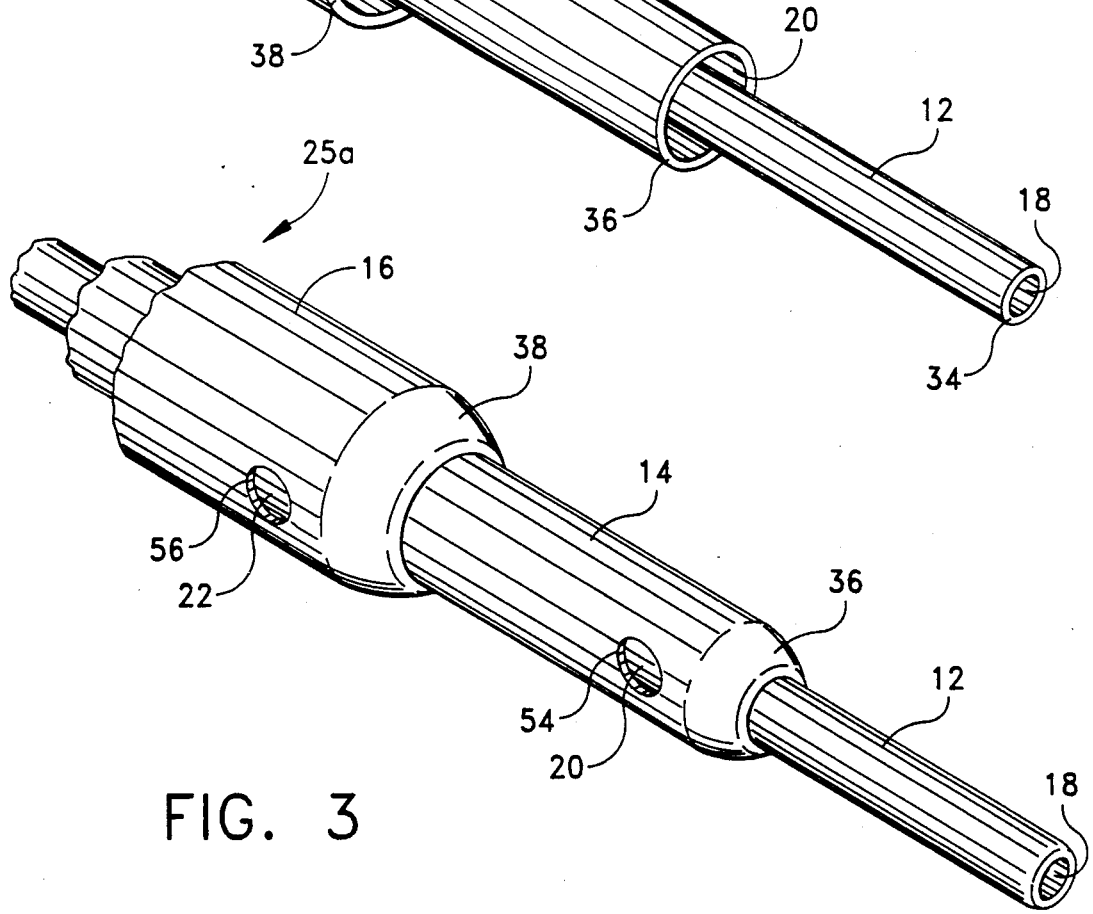
FIG. 3 is a perspective view of an alternative embodiment of the distal end of the multilumen catheter of FIG. 2A.

Referring now to FIG. 3, an alternate embodiment of the distal end 25a of the multilumen catheter 10 is shown. In this embodiment, the distal end 36 of the middle tube 14 is tapered and abuts the inner tube 12 which outwardly extends beyond the middle tube 14. The lumen 20 defined by the middle tube 14 terminates in a side opening 54 slightly upstream from the tapered distal end 36 of the middle tube 14.

Furthermore, the distal end 38 of the outer tube 16 is tapered and abuts the middle tube 14. The lumen 22 defined by the outer tube 16 terminates in a side opening 56 slightly upstream from the tapered distal end 38 of the outer tube 16.

In accordance with the present invention, the side openings 54, 56 enable lumens 20, 22 to aspirate fluids from the patient as well as deliver fluids to the patient. The lumen 18 defined by the inner tube 12 may serve to deliver fluids or to monitor blood pressure.

Figure 4:
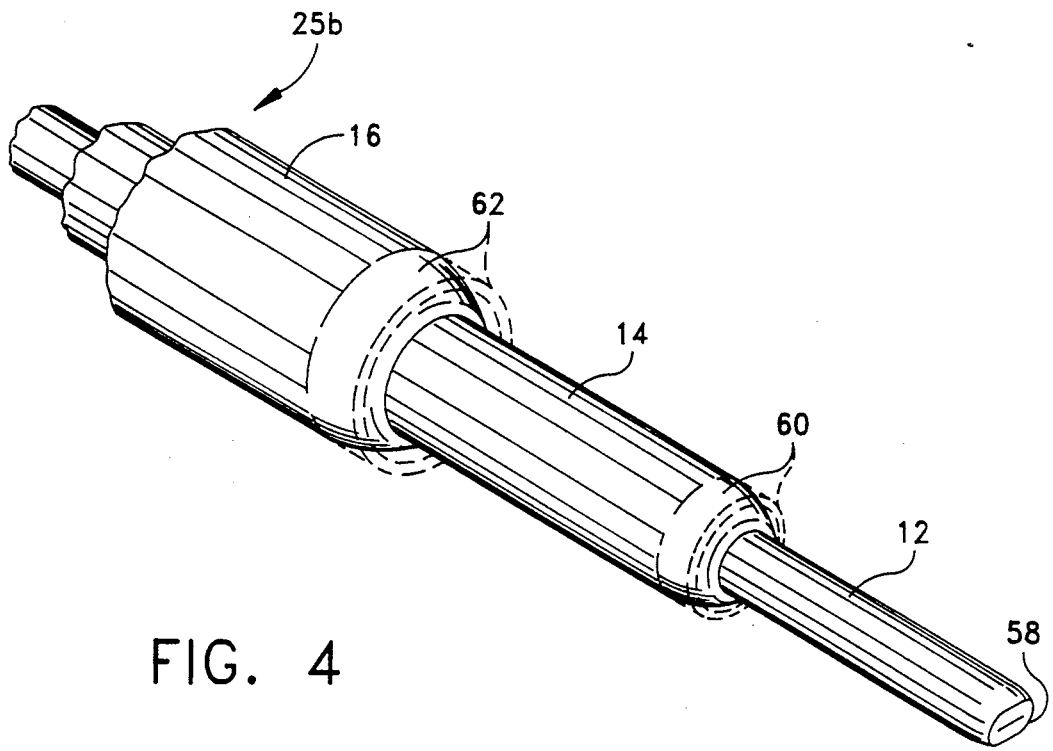
FIG. 4 is a perspective view of another embodiment of the distal end of the multilumen catheter of FIG. 2A.

Referring now to FIG. 4, another embodiment of the distal end 25b of the multilumen catheter is shown. In this embodiment, inner tube 12, the middle tube 14 and the outer tube 16 each terminate in tapered flexible tips 58, 60, 62. The flexible tips 58, 60, 62, expand under pressure exerted from fluids flowing through the respective lumens to allow fluids to exit from the lumens into the bloodstream. However, when no fluids are present in any one or more of the lumens, the flexible tips associated with those lumens remain closed. When closed, the tips 58, 60, 62 act as check valves to prevent the backflow of blood through the lumens thereby completely eliminating the possibility of substantial blood loss through the present multilumen catheter.

Figure 5:
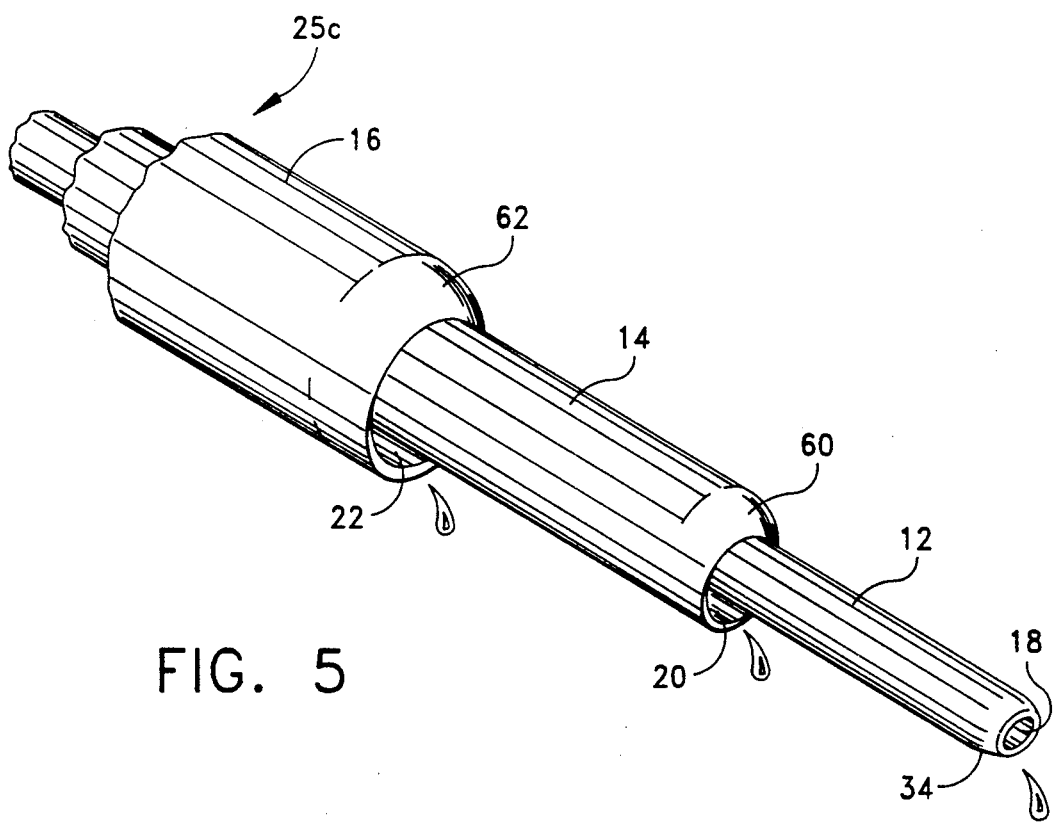
FIG. 5 is a perspective view of yet another embodiment of the distal tip of the multilumen catheter shown in FIG. 2A.

Referring now to FIG. 5, yet another embodiment of the distal end 25c of the multilumen catheter is shown. This embodiment is similar to that shown in FIG. 4 except the inner catheter tube 12 does not terminate in a flexible tip and instead remains open. This enables the lumen 18 defined by the inner tube 12 to be used to monitor blood pressure which would not be possible if the distal end 34 of the inner catheter tube 12 were closed.

In accordance with the present invention, the different embodiments of the distal end of the present multilumen catheter tube as shown in FIGS. 2a-5 may be combined as desired in a single multilumen catheter of the present invention. For example, the outer tube may have a distal end which terminates in a side opening as shown in FIG. 3 while the middle tube terminates in a flexible tip as shown in FIG. 5.

Figure 6:
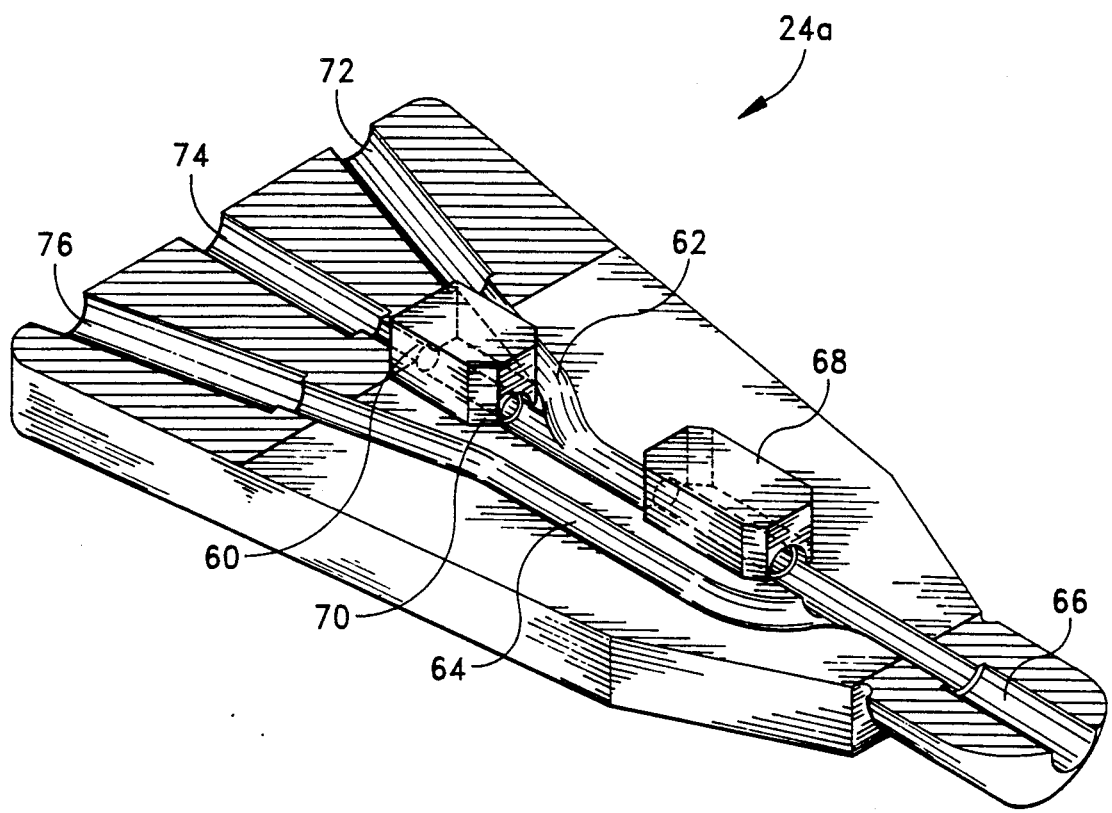
FIG. 6 is a view, partly in section, showing the bottom half of an alternative embodiment of the manifold of the multilumen catheter shown in FIG. 2A.

Referring now to FIG. 6, the bottom half of an alternative embodiment of the manifold 24a is shown. In this embodiment, manifold 24a is molded using known techniques. The manifold 24a secures the respective proximal ends of the catheter tubes. The proximal end of the outer tube is secured at the base 66 of the manifold 24a, the proximal end of the middle tube is secured at the center 68 of the manifold 24a and the proximal end of the inner tube is secured at the top 70 of the manifold 24a. Molded channels 60, 62, 64 separately communicate with the respective lumens defined by each of the catheter tubes. Extension tubes may be molded or otherwise secured into the bottom half of the manifold 24a at channels 72, 74, 76 which are respectively coupled to channels 60, 62, 64 within the manifold.

The inner tube, the middle tube, the outer tube and extension tubing are permanently affixed within the manifold using known techniques. A cooperative top half of the manifold is sealed to the bottom half to provide a sealed, liquid tight unit. Fluids entering or leaving the manifold via the extension tubing communicate with the respective lumens defined by each of the catheter tubes through molded channels 60, 62, 64.

It will be understood that a number of manufacturing techniques known in the art may be used to form the multilumen catheter of the present invention including the various embodiments described above.

The manner of using the multilumen catheter of the present invention is substantially the same as using a conventional multilumen catheter of the prior art, which is well known to those skilled in the art and need not be described in detail.

This invention is not to be limited by what has been particularly shown and described, except as indicated by the appended claims.

What is claimed is:

1. A triple lumen venous catheter comprising:
   an inner venous catheter tube defining a first lumen having a proximal end, and a distal end with the inner catheter tube having a first opening to the first lumen at the proximal end and a second opening to the first lumen at the distal end;
   a middle venous catheter tube defining a second lumen and having a proximal end, a distal end and a cross-section which is greater than the cross-section of the inner tube, the middle tube being disposed concentrically and coaxially with the inner tube, and the distal end of the inner tube extending longitudinally outward from the distal end of the middle tube with the middle catheter tube having a first opening to the second lumen at the proximal end and a second opening to the lumen at the distal end;
   an outer venous catheter tube defining a third lumen and having a proximal end, a distal end and a cross-section which is greater than the cross-section of the middle tube, the outer tube being disposed concentrically and coaxially with the middle tube and the inner tube, and the distal end of the middle tube extending longitudinally outward from the distal end of the outer tube; the outer tube having an outer diameter corresponding to the inner diameter of a patient's vein in which the outer catheter tube is to be inserted and the outer catheter tube having a first opening to the third lumen at the proximal end and a second opening to the third lumen at the distal end;
   a manifold securing and encapsulating each of the proximal ends of the inner, middle and outer venous catheter tubes to provide separate and noncommunicating passages to each of the inner, middle and outer tubes; and
   a plurality of extension tubes coupled to the manifold, each separately coupled to a respective one of the lumens.

2. The triple lumen catheter of claim 1 wherein one of the extension tubes is configured for connection to a fluid transfer device or pressure monitoring means.

3. The triple lumen catheter of claim 2 wherein the manifold includes channels for separately coupling each of the lumens to a corresponding one of the plurality of extension tubes.

4. The triple lumen catheter of claim 1 wherein each of the lumens terminates coextensively with the respective distal end of the inner, middle and outer venous catheter tubes.

5. The triple lumen catheter of claim 1 wherein the distal end of the outer venous catheter tube is tapered and abuts the middle venous catheter tube, and the distal end of the middle venous catheter tube is tapered and abuts the inner venous catheter tube;
   and wherein the second opening of the second lumen is a side opening disposed slightly upstream from the tapered distal end of the middle venous catheter tube, and the second opening of the third lumen is a side opening disposed slightly upstream from the tapered distal end of the outer venous catheter tube.

6. The triple lumen catheter of claim 1 wherein the distal end of the middle venous catheter tube and the distal end of the outer venous catheter tube each terminate in a flexible, tapered tip which expands under the pressure of fluid flowing from the proximal end to the distal end in the respective second and third lumens of the middle and outer venous catheter tubes.

7. The triple lumen catheter of claim 6 wherein the distal end of the inner venous catheter tube terminates in a flexible, tapered tip.

8. The triple lumen catheter of claim 6 wherein each of the flexible tips act as check valves to prevent fluid from entering the first, second and third lumens from the corresponding second openings provided at the corresponding distal ends of the inner, middle and outer venous catheter tubes.

9. The triple lumen catheter of claim 1 wherein the inner, middle and outer venous catheter tubes are made from flexible, sterilizable materials.

10. The triple lumen catheter of claim 9 wherein said materials include polyurethane, silicone, polyvinyl chloride (PVC) and nylon.

11. The triple lumen catheter of claim 9 wherein the inner and middle venous catheter tubes are made from a less rigid material than the outer venous catheter tube.

12. The triple lumen catheter of claim 11 wherein the inner and middle venous catheter tubes are made from polyurethane.

13. The triple lumen catheter of claim 1 wherein the manifold is molded.

14. The triple lumen catheter tube of claim 1 wherein the manifold is made in separate molded sections.

15. The triple lumen catheter tube of claim 14 wherein the separate molded sections are first, second and third hubs;
   the first hub defining a first channel which receives and secures the inner venous catheter tube in fluid-tight communication with said respective extension tubing;
   the second hub defining an annular space which receives and secures the middle venous catheter tube in fluid-tight communication with the respective extension tubing; and
   the third hub defining an annular space which receives and secures the outer venous catheter tube in fluid-tight communication with the respective extension tubing.

16. A multilumen catheter comprising:
   a plurality of concentrically and coaxially disposed venous catheter tubes, each of the plurality of venous catheter tubes defining a lumen and each of the venous catheter tubes having a proximal end and a distal end which extends outwardly from the distal end of the next surrounding venous catheter tube with said multilumen venous catheter having an outer diameter corresponding to the inner diameter of a patient's vein in which the outer catheter tube is to be inserted and each of the plurality of venous catheter tubes having a first opening to the corresponding lumen at the proximal end and a second opening to the corresponding lumen at the distal end;

a like plurality of extension tubes, with a first end of each of said extension tubes coupled to the proximal end of a corresponding one of said lumens defined by the plurality of venous catheter tubes and a second end of each of the extension tubes configured for attachment to utilization means; and a manifold having a like plurality of channels disposed therein with each of the plurality of channels having disposed therein the proximal end of a corresponding one of the plurality of catheter tubes and the coupled first end of the corresponding extension tube, with the manifold securing and encapsulating each of the proximal ends of the plurality of catheter tubes and the corresponding coupled portion of the extension tubing, the manifold providing a separate, non-communicating fluid path between each of the lumens and the respective extension tubing.

17. The triple lumen catheter of claim 1 wherein the proximal end of the inner venous catheter tube extends beyond said proximal end of the middle venous catheter tube.

18. The triple lumen catheter of claim 17 wherein the proximal end of said middle venous catheter tube extends beyond the proximal end of the outer venous catheter tube.

* * * * *

UNITED STATES PATENT AND TRADEMARK OFFICE
CERTIFICATE OF CORRECTION

PATENT NO. : 5,207,648
DATED : 5/4/93
INVENTOR(S) : James R. Gross

It is certified that error appears in the above-indentified patent and that said Letters Patent is hereby corrected as shown below:

Cover page, after "(22) FILED: "Aug. 19, 1992"
insert: Related U.S. Application Data
(63) Continuation of Ser. No. 07/627,534, Dec. 14, 1990, abandoned Col. 1, before the third line, insert--
This is a continuation of application Serial No. 07/627,534, filed December 14, 1990 and now abandoned.

Signed and Sealed this

Twenty-sixth Day of April, 1994

Attest:

BRUCE LEHMAN

*Attesting Officer*  *Commissioner of Patents and Trademarks*